US012591966B2

(12) United States Patent
Kim et al.

(10) Patent No.: US 12,591,966 B2
(45) Date of Patent: Mar. 31, 2026

(54) METHOD AND APPARATUS FOR ANALYZING BLOOD VESSEL BASED ON MACHINE LEARNING MODEL

(71) Applicant: THE CATHOLIC UNIVERSITY OF KOREA INDUSTRY-ACADEMIC COOPERATION FOUNDATION, Seoul (KR)

(72) Inventors: Namkug Kim, Seoul (KR); Keewon Shin, Gyeonggi-do (KR); Dae-Won Kim, Daejeon (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 310 days.

(21) Appl. No.: 18/209,389

(22) Filed: Jun. 13, 2023

(65) Prior Publication Data

US 2024/0135530 A1    Apr. 25, 2024
US 2024/0233118 A9    Jul. 11, 2024

(30) Foreign Application Priority Data

Oct. 24, 2022    (KR) ........................ 10-2022-0137515

(51) Int. Cl.
   *G06T 7/00*      (2017.01)
   *A61B 6/00*      (2024.01)
       (Continued)

(52) U.S. Cl.
   CPC ............ *G06T 7/0012* (2013.01); *A61B 6/504* (2013.01); *A61B 6/5217* (2013.01); *G06N 20/00* (2019.01);
       (Continued)

(58) Field of Classification Search
   CPC ..................... G06T 7/0012; G06T 7/62; G06T 2207/20081; G06T 2207/30101;
       (Continued)

(56) References Cited

U.S. PATENT DOCUMENTS 6,233,304 B1   5/2001   Hu ........................... A61B 6/03
6,408,201 B1   6/2002   Foo ......................... A61B 5/055
       (Continued)

FOREIGN PATENT DOCUMENTS

CN   108492272    9/2018   ............... G06T 5/00
JP   200295647    4/2002   ............. A61B 5/055
       (Continued)

OTHER PUBLICATIONS

Chamuleau, Steven AJ, et al. "Association between coronary lesion severity and distal microvascular resistance in patients with coronary artery disease." American Journal of Physiology-Heart and Circulatory Physiology 285.5 (2003): H2194-H2200. (Year: 2003).*
       (Continued)

*Primary Examiner* — Sumati Lefkowitz
*Assistant Examiner* — Ryan P Potts
(74) *Attorney, Agent, or Firm* — HAYES SOLOWAY P.C.

(57)        ABSTRACT

An apparatus for analyzing a blood vessel includes a processor configured to detect a blood vessel area corresponding to the blood vessel and a stenosis area corresponding to a stenosed portion of the blood vessel, based on a machine learning model, from a blood vessel image, determine a partial area of the blood vessel area to be a comparison area for the stenosis area, based on a length of the stenosis area, and calculate a stenosis score indicating a degree of stenosis of a blood vessel of the stenosis area compared to a blood vessel of the comparison area.

18 Claims, 6 Drawing Sheets

(51) Int. Cl.

| | |
|---|---|
| *A61B 6/50* | (2024.01) |
| *G06N 20/00* | (2019.01) |
| *G06T 7/11* | (2017.01) |
| *G06T 7/62* | (2017.01) |
| *G06V 10/20* | (2022.01) |
| *G06V 40/14* | (2022.01) |

(52) U.S. Cl.
CPC .................. *G06T 7/11* (2017.01); *G06T 7/62* (2017.01); *G06V 10/20* (2022.01); *G06V 40/14* (2022.01); *G06T 2207/20081* (2013.01); *G06T 2207/30101* (2013.01); *G06T 2207/30172* (2013.01)

(58) Field of Classification Search
CPC ......... G06T 2207/30172; G06T 7/0016; G06T 7/11; A61B 6/5217; A61B 5/055; A61B 6/504; G06N 20/00; G06V 10/20; G06V 40/14
See application file for complete search history.

(56) References Cited

U.S. PATENT DOCUMENTS

| | | | |
|---|---|---|---|
| 10,098,602 B2 | 10/2018 | Lee ........................... | A61B 6/00 |
| 11,382,569 B2 | 7/2022 | Grady ....................... | A61B 5/00 |
| 11,756,195 B2 | 9/2023 | Kweon ................... | A61B 34/10 |
| 2015/0342551 A1* | 12/2015 | Lavi ....................... | G16H 50/50 |
| | | | 600/407 |
| 2018/0243033 A1* | 8/2018 | Tran ..................... | A61B 5/7264 |
| 2021/0085397 A1* | 3/2021 | Passerini ............. | A61B 5/7278 |
| 2021/0217165 A1* | 7/2021 | Min ........................ | A61B 6/504 |
| 2021/0290076 A1* | 9/2021 | Siemionow ............... | G06T 7/12 |
| 2022/0151580 A1* | 5/2022 | Itu .......................... | G06T 7/0012 |
| 2023/0368398 A1* | 11/2023 | Figueroa-Alvarez ..... | G06T 5/70 |

FOREIGN PATENT DOCUMENTS

| | | | | |
|---|---|---|---|---|
| JP | 2002531199 | | 9/2002 | ............... A61B 6/03 |
| JP | 2003310601 A | * | 11/2003 | |
| KR | 102358996 | | 1/2002 | ............... A61B 5/00 |
| KR | 1020150058948 | | 5/2015 | ............... A61B 6/03 |
| KR | 1020220037422 | | 3/2022 | ............... A61B 6/00 |
| KR | 1020220075126 | | 6/2022 | ............... A61B 8/08 |

OTHER PUBLICATIONS

Shin et al., "Deep learning-based quantitative image analysis for detecting coronary artery stenosis, calcification, and vulnerable plaque in coronary computed tomograhy angiography", The 20th Asian Oceanian Congress of Radiology in conjunction with the 78th Annual Meeting of the Korean Society of Radiology, Sep. 20, 2022-Sep. 24, 2022, 36 pages.

* cited by examiner

1

METHOD AND APPARATUS FOR ANALYZING BLOOD VESSEL BASED ON MACHINE LEARNING MODEL

CROSS-REFERENCE TO RELATED APPLICATION(S)

This application claims the priority benefit of Korean Patent Application No. 10-2022-0137515 filed on Oct. 24, 2022, in the Korean Intellectual Property Office, the disclosure of which is incorporated herein by reference for all purposes.

BACKGROUND

1. Field

One or more embodiments relate to a method of analyzing a blood vessel based on a machine learning model.

2. Description of Related Art

A medical image processing apparatus may refer to equipment for obtaining the internal structure of a subject. The medical image processing apparatus may be a non-invasive examination device and may capture and process an image of the structural details, internal organs, and fluid flows of a body and display the image to a user. The user, such as a doctor, may diagnose the health condition and disease of a patient by using a medical image output from the medical image processing apparatus. Such a device for capturing and processing a medical image may include a magnetic resonance imaging (MRI) device, a computed tomography (CT) device, an X-ray device, or an ultrasound device, and the medical image processing apparatus may generate a medical image by processing captured image data.

The CT device of the medical image processing apparatus may provide a cross-sectional image for the subject and may have the advantage of representing the internal structure (e.g., kidneys, lungs, and other organs) of the subject without them overlapping with one another compared to a general X-ray device.

However, blood vessels, of which the size is several millimeters (mm), may not be accurately captured because a resolution of a CT image is approximately 0.7 mm. In addition, some blood vessels, for example, coronary arteries, may move while being captured due to heartbeat. There may be various artifacts, such as a motion artifact, in a restored CT image due to such movement.

An abnormal blood vessel may need to be accurately read in a medical image for diagnosing coronary artery stenosis, cardiovascular diseases, or other blood vessel-related diseases. However, the accurate reading of an image and diagnosis based thereon may not be readily available due to the small size of the blood vessels and the movement of the blood vessels while being captured as described above.

SUMMARY

According to an aspect, a method performed by an apparatus for analyzing a blood vessel includes detecting a blood vessel area corresponding to the blood vessel and a stenosis area corresponding to a stenosed portion of the blood vessel, based on a machine learning model, from a blood vessel image. The method may further include determining a partial area of the blood vessel area to be a comparison area for the stenosis area, based on the length of the stenosis area. The method may further include calculating a stenosis score indicating a degree of stenosis of a blood vessel of the stenosis area compared to a blood vessel of the comparison area, based on a distribution of blood vessel diameters in a longitudinal direction of the blood vessel in the blood vessel area.

The detecting the blood vessel area and the stenosis area may include detecting an area including a blood vessel diameter decreasing in the longitudinal direction of the blood vessel as the comparison area in an area different from the stenosis area of the blood vessel area.

The determining the comparison area may include determining another partial centerline based on a partial reference line corresponding to the stenosis area of a reference line of the blood vessel. The determining the comparison area may further include determining an area corresponding to the determined other partial reference line to be the comparison area.

The determining the comparison area may further include determining the comparison area corresponding to a normal blood vessel adjacent to the stenosed portion of the stenosis area of the blood vessel area.

The determining the comparison area may further include determining a first area and a second area each on respective sides of the stenosis area in the longitudinal direction of the blood vessel to be the comparison area.

The determining the comparison area may further include determining the first area corresponding to a more proximal blood vessel than the blood vessel of the stenosis area and the second area corresponding to a more distal blood vessel than the blood vessel of the stenosis area to be the comparison area.

The determining the comparison area may further include determining the first area and the second area including a median value of a blood vessel diameter less than a median value of a blood vessel diameter of the first area to be the comparison area.

The calculating the stenosis score may include extracting blood vessel diameters corresponding to the stenosis area and the comparison area from the distribution of the blood vessel diameters. The calculating the stenosis score may further include calculating the stenosis score by using the extracted blood vessel diameters.

The calculating the stenosis score may further include determining a reference vessel diameter estimated as a diameter of a normal blood vessel in the stenosis area, based on the distribution of the blood vessel diameters in the comparison area. The calculating the stenosis score may further include determining a stenosed blood vessel diameter calculated in the stenosis area, based on the distribution of the blood vessel diameters in the stenosis area. The calculating the stenosis score may further include calculating the stenosis score based on a comparison result of the reference vessel diameter and the stenosed blood vessel diameter.

The calculating the stenosis score may further include extracting a first blood vessel diameter from a partial distribution for a first area of the comparison area of the distribution of the blood vessel diameters. The calculating the stenosis score may further include extracting a second blood vessel diameter from a partial distribution for a second area of the comparison area of the distribution of the blood vessel diameters. The calculating the stenosis score may further include calculating a reference vessel diameter corresponding to a normal blood vessel, based on the first blood vessel diameter and the second blood vessel diameter. The calculating the stenosis score may further include extracting a minimum value of a partial distribution for the stenosis area of the distribution of the blood vessel diameters as a stenosed blood vessel diameter corresponding to the stenosis area. The calculating the stenosis score may further include calculating the stenosis score based on a comparison result of the calculated reference vessel diameter and the extracted stenosed blood vessel diameter.

The method may further include detecting a calcification area of the blood vessel area based on a pixel value of the blood vessel image. The method may further include calculating a calcification score indicating a degree of calcification of the blood vessel, based on a ratio of the calcification area to the blood vessel area.

The method may further include outputting a graphic representation indicating the calcification area to the blood vessel image.

The method may further include detecting a plaque area corresponding to a vulnerable plaque, together with the blood vessel area, by applying the machine learning model to the blood vessel image.

According to another aspect, an apparatus for analyzing a blood vessel includes a processor configured to detect a blood vessel area corresponding to the blood vessel and a stenosis area corresponding to a stenosed portion of the blood vessel, based on a machine learning model, from a blood vessel image, determine a partial area of the blood vessel area to be a comparison area for the stenosis area, based on a length of the stenosis area, and calculate a stenosis score indicating a degree of stenosis of a blood vessel of the stenosis area compared to a blood vessel of the comparison area.

The processor may detect an area including a blood vessel diameter decreasing in the longitudinal direction of the blood vessel as the comparison area in an area different from the stenosis area of the blood vessel area.

The processor may determine another partial centerline based on a partial reference line corresponding to the stenosis area of a reference line of the blood vessel. The processor may determine an area corresponding to the determined other partial reference line to be the comparison area.

The processor may determine the comparison area corresponding to a normal blood vessel adjacent to the stenosed portion of the stenosis area of the blood vessel area.

The processor may determine a first area and a second area each on respective sides of the stenosis area in the longitudinal direction of the blood vessel to be the comparison area.

The processor may extract blood vessel diameters corresponding to the stenosis area and the comparison area from the distribution of the blood vessel diameters. The processor may calculate the stenosis score by using the extracted blood vessel diameters.

The processor may determine a reference vessel diameter estimated as a diameter of a normal blood vessel in the stenosis area, based on the distribution of the blood vessel diameters in the comparison area. The processor may determine a stenosed blood vessel diameter calculated in the stenosis area, based on the distribution of the blood vessel diameters in the stenosis area. The processor may calculate the stenosis score based on a comparison result of the reference vessel diameter and the stenosed blood vessel diameter.

The processor may extract a first blood vessel diameter from a partial distribution for a first area of the comparison area of the distribution of the blood vessel diameters. The processor may extract a second blood vessel diameter from a partial distribution for a second area of the comparison area of the distribution of the blood vessel diameters. The processor may calculate a reference vessel diameter corresponding to a normal blood vessel, based on the first blood vessel diameter and the second blood vessel diameter. The processor may extract a minimum value of a partial distribution for the stenosis area of the distribution of the blood vessel diameters as a stenosed blood vessel diameter corresponding to the stenosis area. The processor may calculate the stenosis score based on a comparison result of the calculated reference vessel diameter and the extracted stenosed blood vessel diameter.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the present disclosure will become apparent and more readily appreciated from the following description of example embodiments, taken in conjunction with the accompanying drawings of which.

DETAILED DESCRIPTION

Figure 1:
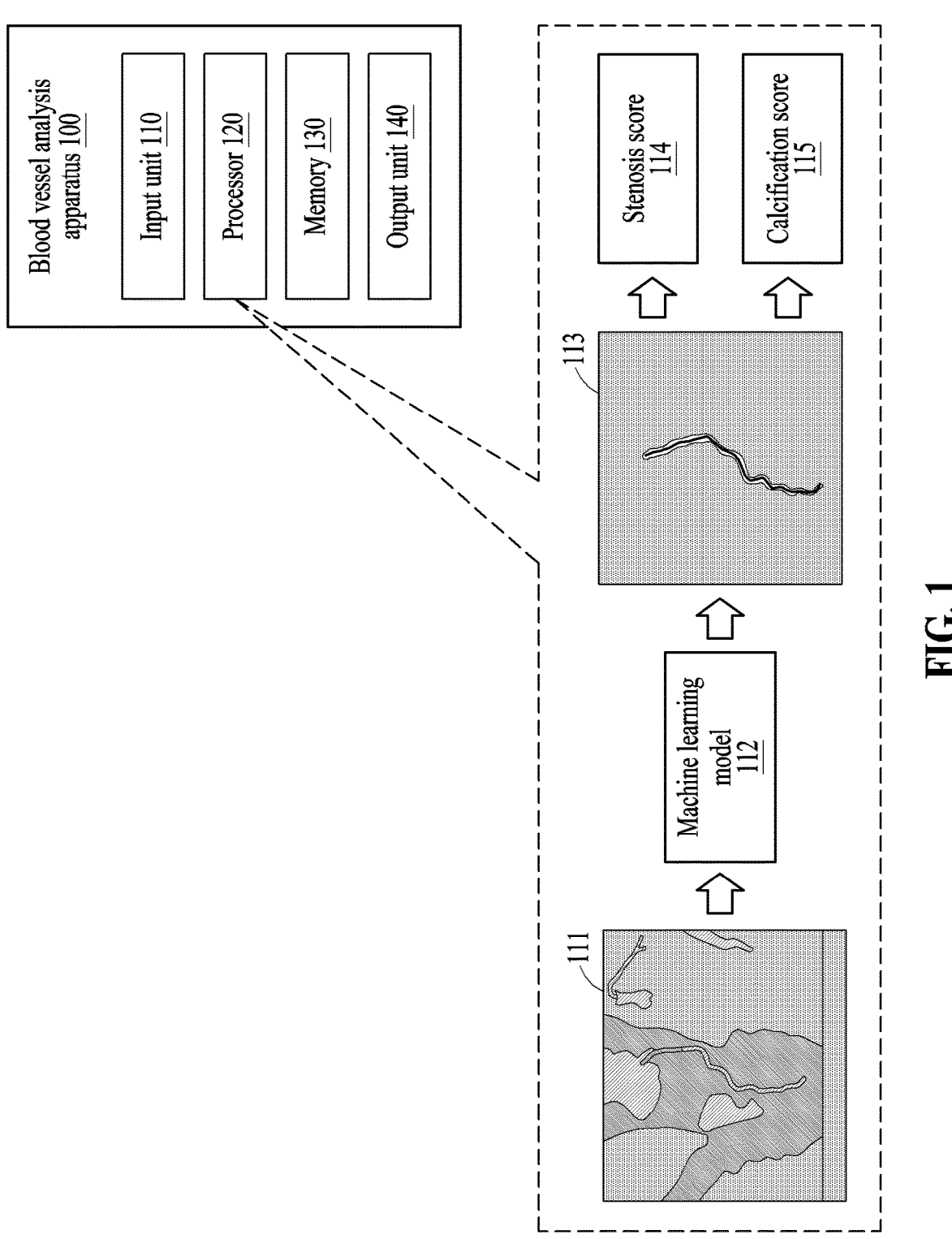
FIG. 1 is a diagram illustrating a blood vessel analysis apparatus according to an embodiment.

The following detailed structural or functional description is provided as an example only and various alterations and modifications may be made to the examples. Here, examples are not construed as limited to the disclosure and should be understood to include all changes, equivalents, and replacements within the idea and the technical scope of the disclosure.

Terms, such as first, second, and the like, may be used herein to describe various components. Each of these terminologies is not used to define an essence, order or sequence of a corresponding component but used merely to distinguish the corresponding component from other component(s). For example, a first component may be referred to as a second component, and similarly the second component may also be referred to as the first component.

It should be noted that if it is described that one component is "connected", "coupled", or "joined" to another component, a third component may be "connected", "coupled", and "joined" between the first and second components, although the first component may be directly connected, coupled, or joined to the second component.

The singular forms "a", "an", and "the" are intended to include the plural forms as well, unless the context clearly indicates otherwise. It will be further understood that the terms "comprises/including" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art and are not to be interpreted in an idealized or overly formal sense unless expressly so defined herein.

Hereinafter, embodiments will be described in detail with reference to the accompanying drawings. When describing the embodiments with reference to the accompanying drawings, like reference numerals refer to like elements and a repeated description related thereto will be omitted.

FIG. 1 is a diagram illustrating a blood vessel analysis apparatus according to an embodiment.

According to an embodiment, a blood vessel analysis apparatus 100 may process a blood vessel image by using a machine learning model. The blood vessel analysis apparatus 100 may obtain at least one of a stenosis score, a calcification score, and a plaque area by processing the blood vessel image.

For example, the blood vessel may calculate the stenosis score from the blood vessel image. The stenosis score may include a score indicating the degree of stenosis of a blood vessel in at least a portion of a blood vessel area compared to a normal blood vessel.

For example, the blood vessel analysis apparatus 100 may calculate the calcification score from the blood vessel image. The calcification score may include a score indicating the degree of calcification of a blood vessel. Calcification may mean that calcium excessively deposits until the tissues or organs of a body harden like a stone. Calcium compounds may be in blood vessels, joints, breasts, and various other areas of the body and may have the possibility of progressing to cancer in some cases. The calcification of a blood vessel may mean that calcium builds up in a muscle layer, that is, a middle layer of three layers of a blood vessel wall. A blood vessel may lose elasticity as the blood vessel is calcified. As the elasticity of the blood vessel decreases, blood flow may become not smooth, and the possibility of a blood clot may increase.

For example, the blood vessel analysis apparatus 100 may detect the plaque area from the blood vessel image. The plaque area may include, for example, a partial area corresponding to a vulnerable plaque of the blood vessel area. The vulnerable plaque may be a plaque having a risk of forming a blood clot when being exposed to a pertinent stimulus and may include a plaque with a lipid-rich core and a fibrous cap where macrophage infiltration is active, according to histological research. For example, the vulnerable plaque may include a plaque that is prone to plaque rupture or thrombosis and a plaque where severe stenosis occurs due to the rapid progress of a lesion.

According to an embodiment, the blood vessel analysis apparatus 100 may include an input unit 110, a processor 120, and a memory 130.

The input unit 110 may obtain a blood vessel image capturing a blood vessel of a patient. According to an embodiment, an external device separated from the blood vessel analysis apparatus 100 may generate data corresponding to the blood vessel image. The input unit 110 may include an interface for receiving the blood vessel image by wire and/or wirelessly from the external device. According to an embodiment, when a device for generating data corresponding to a blood vessel image is integrated into the blood vessel analysis apparatus 100, the input unit 110 may obtain the blood vessel image by generating the data corresponding to the blood vessel image.

The processor may obtain at least one of a stenosis score 114, a calcification score 115, and a plaque area (not shown) by analyzing a blood vessel image 111 obtained through the input unit 110. For example, the processor 120 may detect a blood vessel area and a stenosis area by applying a machine learning model 112 to the blood vessel image 111. The processor 120 may calculate the stenosis score 114 based on the detected blood vessel area and the stenosis area. For example, the processor 120 may calculate the calcification score 115 indicating the degree of calcification of the blood vessel area detected based on the machine learning model 112. For example, the processor 120 may detect the plaque area together with the blood vessel area by applying the blood vessel image 111 to the machine learning model 112.

The memory 130 may store the blood vessel image 111 obtained through the input unit 110. The memory 130 may store instructions for analyzing the blood vessel image 111. The memory 130 may store the stenosis score 114 and/or the calcification score 115 calculated by analyzing the blood vessel image 111.

An output unit 140 may display the blood vessel image 111. The output unit 140 may output a graphic representation indicating at least one of the blood vessel area, the calcification area, and the plaque area to the blood vessel image 111. According to an embodiment, the output unit 140 may be implemented as a display.

Figure 2:
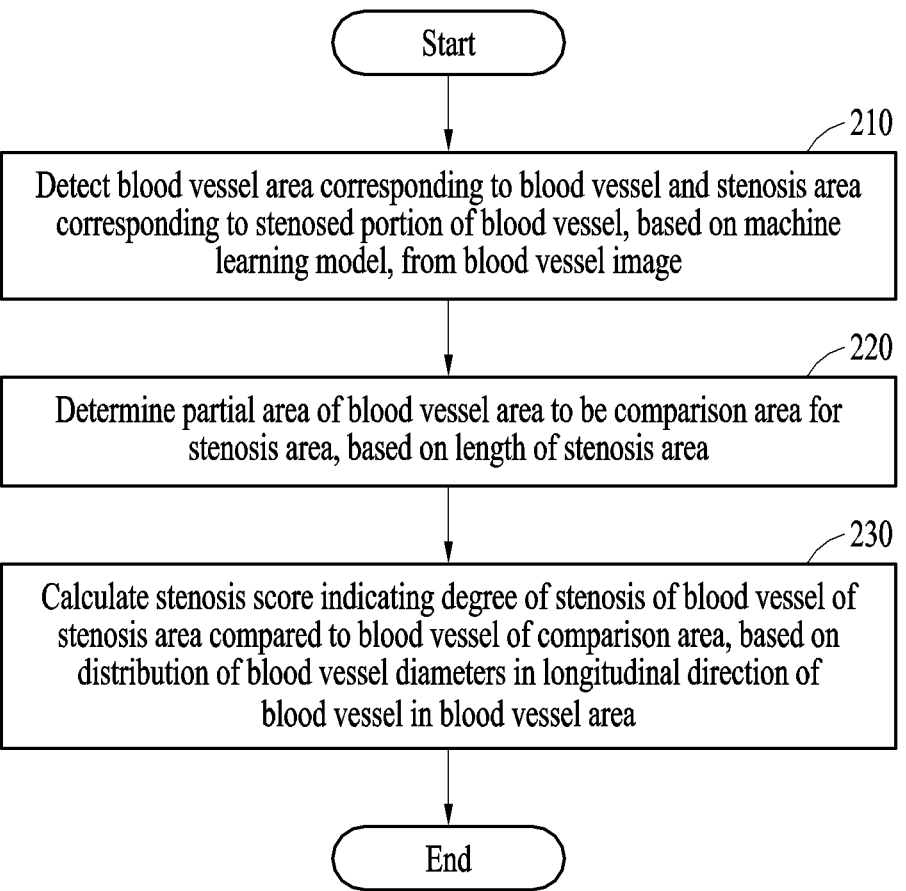
FIG. 2 is a diagram illustrating an operation of calculating a stenosis score based on a machine learning model by the blood vessel analysis apparatus according to an embodiment.

FIG. 2 is a diagram illustrating an operation of calculating a stenosis score based on a machine learning model by the blood vessel analysis apparatus according to an embodiment.

The blood vessel analysis apparatus (e.g., the blood vessel analysis apparatus 100 of FIG. 1) according to an embodiment may detect a blood vessel area and a stenosis area corresponding to a stenosed portion of a blood vessel from a blood vessel image by using the machine learning model. The stenosis area may be detected as a partial area of the blood vessel area. The blood vessel analysis apparatus may calculate a stenosis score indicating the degree of stenosis of the stenosed portion of the blood vessel compared to another portion by analyzing the detected blood vessel area and the stenosis area.

In operation 210, the blood vessel analysis apparatus may detect the blood vessel area and the stenosis area, based on the machine learning model, from the blood vessel image. The blood vessel area may correspond to a blood vessel displayed in the blood vessel image.

The blood vessel image may include a medical image displaying blood vessels. For example, the blood vessel image may include at least one of a computed tomography (CT) image, a magnetic resonance imaging (MRI) image, an X-ray image, and a positron emission tomography (PET) image. The blood vessel image may include a medical image obtained by performing preprocessing on a target blood vessel of the blood vessels displayed in the medical image. The target blood vessel may be a portion (e.g., one branch) of a blood vessel to be a target of analysis when the blood vessel displayed in the medical image has one or more branches. For example, the target blood vessel may be a main blood vessel selected by medical personnel and a coronary artery may be selected. The blood vessel image may be obtained by processing the medical image such that the target blood vessel of the blood vessels displayed in the medical image is emphasized, and other blood vessels, besides the target blood vessel, are blurred. For example, the blood vessel image may be obtained by increasing a contrast between an area corresponding to the target blood vessel and another area and by decreasing a contrast between the other blood vessels, besides the target blood vessel, and the other area (e.g., an area corresponding to an organ). According to an embodiment, the blood vessel image may be a multiplanar reformation (MPR) image obtained by converting the medical image to a reference plane. According to an embodiment, the blood vessel analysis apparatus may perform blood vessel analysis rapidly with a small throughput by analyzing a blood vessel based on the medical image processed such that the target blood vessel is emphasized, and the other blood vessels are blurred. The blood vessel analysis apparatus may be used for screening because of the high sensitivity of the blood vessel analysis apparatus in a situation (e.g., an emergency) clinically requiring rapid blood vessel analysis.

The machine learning model may include a segmentation model that is trained to detect a blood vessel area corresponding to a blood vessel by being applied to the blood vessel image. The machine learning model may be trained to further detect a stenosis area corresponding to a stenosed portion of the blood vessel together with the blood vessel area. As described below with reference to FIG. 6, the machine learning model may be trained to further detect a plaque area corresponding to a vulnerable plaque together with the blood vessel area. According to an embodiment, the machine learning model may be implemented as a neural network model. For example, the machine learning model may be implemented as a model based on a U-Net.

The stenosis area may correspond to a stenosed portion of a blood vessel. According to an embodiment, the stenosis area may be detected as a partial area of a blood vessel area. The blood vessel area may be an area separated from the stenosis area and may include a partial area (e.g., the remaining area excluding the stenosis area from the blood vessel area) corresponding to a normal blood vessel.

According to an embodiment, the blood vessel analysis apparatus may detect a blood vessel area having a blood vessel diameter decreasing in a longitudinal direction of a blood vessel in an area different from the stenosis area of the blood vessel area. The area (e.g., an area corresponding to the normal blood vessel) different from the stenosis area of the blood vessel area detected based on the machine learning model may have the blood vessel diameter decreasing in the longitudinal direction of the blood vessel. A portion (e.g., a normal blood vessel portion) different from the stenosed portion (e.g., a stenosed blood vessel portion) of the blood vessel displayed in the blood vessel image may have a blood vessel diameter decreasing in the longitudinal direction of the blood vessel. The stenosed portion may have a blood vessel diameter less than that of at least some of the portion independently of (or regardless of) the tendency of the blood vessel diameter of the portion. For example, the stenosed portion may have the blood vessel diameter deviating from the tendency of the blood vessel diameter of the portion.

In operation 220, the blood vessel analysis apparatus may determine a partial area of the blood vessel area to be a comparison area for the stenosis area. The blood vessel analysis apparatus may determine the comparison area based on the length of the stenosis area. For example, the blood vessel analysis apparatus may determine the comparison area having a length based on the length of the stenosis area.

According to an embodiment, the blood vessel analysis apparatus may determine a reference line for the blood vessel area. The reference line may be a reference line of a blood vessel and may include a line in the longitudinal direction of the blood vessel. The reference line of the blood vessel may include, for example, a centerline having center points of the lumen of the blood vessel. The blood vessel analysis apparatus may determine another partial centerline based on a partial reference line corresponding to the stenosis area of the reference line for the blood vessel area. The partial reference line corresponding to the stenosis area may be a portion of the reference line for the stenosed portion (e.g., the stenosed blood vessel portion) of the blood vessel. The partial reference line corresponding to the stenosis area may be a portion of the reference line included in the stenosis area of reference lines. For example, the blood vessel analysis apparatus may determine at least another partial reference line adjacent to the partial reference line and having the same length as the length of the partial reference line. The blood vessel analysis apparatus may determine an area corresponding to the determined other partial reference line to be the comparison area.

According to an embodiment, the blood vessel analysis apparatus may determine a comparison area corresponding to a normal blood vessel adjacent to the stenosed portion of the stenosis area of the blood vessel area. For example, the blood vessel analysis apparatus may determine some of an area (e.g., the area corresponding to the normal blood vessel) different from the stenosis area of the blood vessel area to be the comparison area. Since the comparison area is an area for the normal blood vessel adjacent to the stenosed portion, the comparison area may be determined to be an area for a normal blood vessel that is highly likely to be displayed in the blood vessel image if the stenosed blood vessel portion in the stenosis area were not stenosed (or if it were the normal blood vessel).

According to an embodiment, the blood vessel analysis apparatus may determine a first area and a second area each on respective sides of the stenosis area in the longitudinal direction of the blood vessel to be the comparison area. For example, the first area may correspond to a more proximal blood vessel than the blood vessel of the stenosis area. The proximal blood vessel may be a blood vessel closer to the center (e.g., a heart) of a body than a comparison reference (e.g., the blood vessel of the stenosis area). The second area may correspond to a more distal blood vessel than the blood vessel of the stenosis area. The distal blood vessel may be a blood vessel farther from the center (e.g., the heart) of the body than the comparison reference (e.g., the blood vessel of the stenosis area). For example, the blood vessel analysis apparatus may determine the first area and the second area having a median value of the blood vessel diameter less than the median value of the blood vessel diameter of the first area to be the comparison area. The median value of the blood vessel diameter of the second area may be less than the median value of the blood vessel diameter of the first area. The diameter of a blood vessel may decrease as the blood vessel is farther from the center (e.g., the heart) of the body. When the first area is a more proximal blood vessel to the center (e.g., the heart) of the body than the second area, the median value of the blood vessel diameter of the first area may be greater than the median value of the blood vessel diameter of the second area.

The example of determining the comparison area is described below with reference to FIG. 3.

In operation 230, the blood vessel analysis apparatus may calculate the stenosis score based on the distribution of blood vessel diameters in the longitudinal direction of the blood vessel in the blood vessel area. The stenosis score may indicate the degree of stenosis of the blood vessel of the stenosis area compared to a blood vessel of the comparison area. For example, the blood vessel analysis apparatus may determine a reference blood vessel diameter from the distribution of blood vessel diameters in the comparison area. The blood vessel analysis apparatus may determine a stenosed blood vessel diameter from the distribution of blood vessel diameters in the stenosis area. The blood vessel analysis apparatus may calculate the stenosis score based on the reference blood vessel diameter and the stenosed blood vessel diameter. The example of calculating the stenosis score is described below with reference to FIG. 4.

Figure 3:
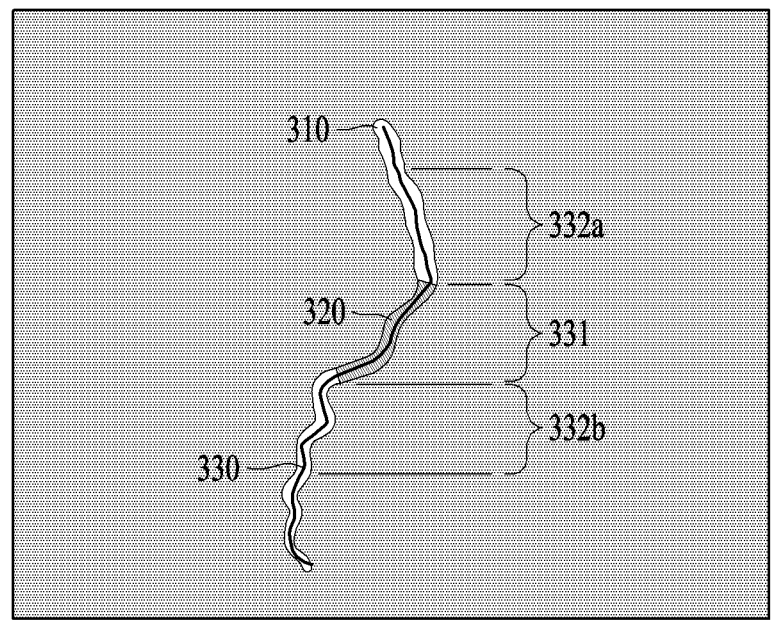
FIG. 3 is a diagram illustrating an operation of determining a comparison area by using a reference line of a blood vessel by the blood vessel analysis apparatus according to an embodiment.

FIG. 3 is a diagram illustrating an operation of determining a comparison area by using a reference line of a blood vessel by the blood vessel analysis apparatus according to an embodiment.

The blood vessel analysis apparatus according to an embodiment may detect a blood vessel area 310 and a stenosis area 320 from a blood vessel image based on a machine learning model.

The blood vessel analysis apparatus may determine a reference line 330 of a blood vessel based on the blood vessel area 310. As illustrated in FIG. 3, for example, the blood vessel analysis apparatus may determine the reference line 330 in the blood vessel area 310 to be a centerline. The centerline may be a line having center points of the lumen of the blood vessel in the blood vessel area 310.

The blood vessel analysis apparatus may determine a partial reference line 331 for the stenosis area 320 of the reference line 330 for the blood vessel area 310. The partial reference line 331 may be determined to be a portion belonging to the stenosis area 320 of the reference line 330. The partial reference line 331 may include a partial reference line for a stenosed portion of the blood vessel of the blood vessel area 310.

The blood vessel analysis apparatus may determine another partial reference line based on the partial reference line 331. The other partial reference line may include a partial reference line for a portion (e.g., a normal blood vessel portion) different from the stenosed portion of the blood vessel of the blood vessel area 310. As illustrated in FIG. 3, for example, the blood vessel analysis apparatus may determine a first partial reference line 332a and a second partial reference line 332b to be the other partial reference line, based on the partial reference line 331.

For example, the blood vessel analysis apparatus may determine another partial reference line adjacent to the partial reference line 331. For example, the blood vessel analysis apparatus may determine at least one of the first partial reference line 332a and the second partial reference line 332b that are adjacent to the partial reference line 331 to be the other partial reference line.

For example, the blood vessel analysis apparatus may determine the other partial reference line having a length (e.g., the same length as the partial reference line 331) based on the length of the partial reference line 331. For example, the blood vessel analysis apparatus may determine the first partial reference line 332a and the second partial reference line 332b that have the same length as the length of the partial reference line 331 to be the other partial reference lines.

For example, the blood vessel analysis apparatus may determine other reference lines that are each on respective sides of the partial reference line 331 in a longitudinal direction (or in a longitudinal direction of the centerline of the blood vessel) of the blood vessel. For example, the blood vessel analysis apparatus may determine the first partial reference line 332a and the second partial reference line 332b each on respective sides of the partial reference line 331 in the longitudinal direction of the blood vessel to be the other partial reference lines. For example, the first partial reference line 332a may correspond to a more proximal blood vessel than the partial reference line 331 (or a stenosed portion of the blood vessel corresponding to the partial reference line 331). The second partial reference line 332b may correspond to a more distal blood vessel than the partial reference line 331 (or the stenosed portion of the blood vessel corresponding to the partial reference line 331).

The blood vessel analysis apparatus may determine an area corresponding to the determined other partial reference line to be the comparison area. The blood vessel analysis apparatus may determine a portion (e.g., a normal blood vessel portion) different from the stenosed portion of the blood vessel to be the comparison area.

For example, the blood vessel analysis apparatus may determine a comparison area corresponding to a normal blood vessel adjacent to the stenosed portion of the stenosis area, based on the other partial reference line adjacent to the partial reference line 331. For example, the blood vessel analysis apparatus may determine the comparison area having a length based on the length of the stenosis area, based on another partial reference line having a length based on the length of the partial reference line 331.

For example, the blood vessel analysis apparatus may determine the first area and the second area each on respective sides of the stenosis area in the longitudinal direction of the blood vessel to be the comparison area, based on other partial reference lines (e.g., the first partial reference line 332a and the second partial reference line 332b) each on respective sides of the partial reference line 331 in the longitudinal direction of the blood vessel. For example, the blood vessel analysis apparatus may determine the first area corresponding to the first partial reference line 332a and the second area corresponding to the second partial reference line 332b to be the comparison area. Since the first partial reference line 332a corresponds to a more proximal blood vessel than the stenosed blood vessel portion, the first area may correspond to a more proximal blood vessel than the stenosis area 320. Since the second partial reference line 332b corresponds to a more distal blood vessel than the stenosed blood vessel portion, the second area may correspond to a more distal blood vessel than the stenosis area 320.

Figure 4:
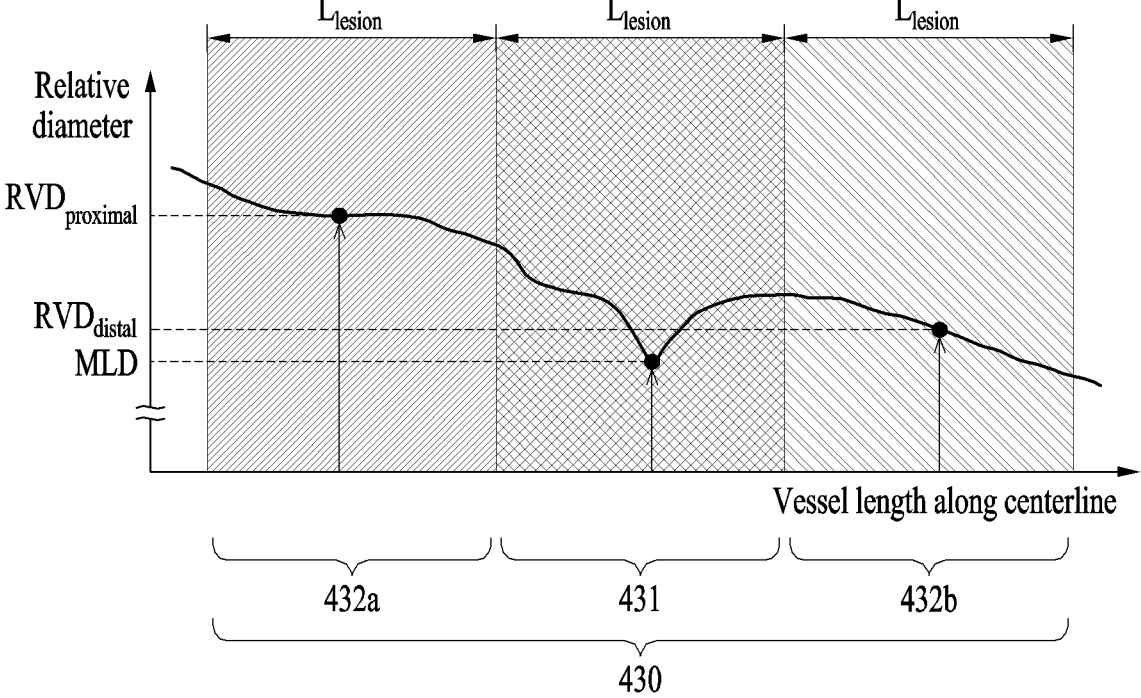
FIG. 4 is a diagram illustrating an operation of calculating a stenosis score based on a distribution of blood vessel diameters by the blood vessel analysis apparatus according to an embodiment.

FIG. 4 is a diagram illustrating an operation of calculating a stenosis score based on a distribution of blood vessel diameters by the blood vessel analysis apparatus according to an embodiment.

The blood vessel analysis apparatus according to an embodiment may detect a blood vessel area and a stenosis area by using a machine learning model and may determine a comparison area for the stenosis area.

The blood vessel analysis apparatus may calculate the stenosis score indicating the degree of stenosis of a blood vessel of the stenosis area compared to a blood vessel of the comparison area. The blood vessel analysis apparatus may calculate the stenosis score based on a distribution 430 of blood vessel diameters in a longitudinal direction of a blood vessel of the blood vessel area. The distribution 430 of blood vessel diameters may have a blood vessel diameter obtained along a reference line of the blood vessel. For example, the blood vessel diameter may be obtained as an area (or a length) where a plane (or a straight line) perpendicular to the reference line of the blood vessel at one point of the reference line of the blood vessel is overlapped with the blood vessel area.

In FIG. 4, the distribution 430 of blood vessel diameters may be the distribution of blood vessel diameters in at least some of the blood vessel area. The distribution 430 of blood vessel diameters may include a partial distribution (e.g., a partial distribution 432*a* and a partial distribution 432*b*) for the comparison area and a partial distribution 431 for the stenosis area.

An area (e.g., the comparison area) different from the stenosis area of the blood vessel area may have a blood vessel diameter decreasing in the longitudinal direction of the blood vessel. For example, as illustrated in FIG. 4, in the distribution (e.g., the partial distribution 432*a* and the partial distribution 432*b*) for the comparison area, a blood vessel diameter at a first point of the reference line of the blood vessel may be greater than a blood vessel diameter of a second point that is farther than the first point from the reference line (e.g., a point on the reference line that is closest to the center (e.g., a heart) of a body). The comparison area may include a first area corresponding to a more proximal blood vessel than the stenosis area and a second area corresponding to a more distal blood vessel than the stenosis area. For example, in FIG. 4, the partial distribution 432*a* may be a partial distribution for the first area of the distribution 430 of blood vessel diameters, and the partial distribution 432*b* may be a partial distribution for the second area of the distribution 430 of blood vessel diameters. When the median value of the blood vessel diameter of the second area is less than the median value of the blood vessel diameter of the first area, the median value of the partial distribution 432*b* for the second area may be less than the median value of the partial distribution 432*a* for the first area.

According to an embodiment, the blood vessel analysis apparatus may extract blood vessel diameters corresponding to the stenosis area and the comparison area from the distribution 430 of blood vessel diameters. The blood vessel apparatus may calculate a stenosis score by using the extracted blood vessel diameters.

According to an embodiment, the blood vessel analysis apparatus may determine a reference vessel diameter (RVD) based on the distribution of blood vessel diameters in the comparison area. The RVD may be a diameter of a blood vessel estimated as a diameter of a normal blood vessel in the stenosis area. For example, the RVD may include a diameter of a blood vessel estimated to be obtained if the blood vessel of the stenosis area were not stenosed (or if there were normal blood vessels in the stenosis area). Since the blood vessel of the stenosis area is a stenosed blood vessel, the RVD may be determined based on the distribution of blood vessel diameters in an area (e.g., the comparison area) corresponding to the normal blood vessel different from the stenosis area.

For example, the blood vessel analysis apparatus may determine the RVD from the distribution 430 of blood vessel diameters in the comparison area including the first area and the second area.

The blood vessel analysis apparatus may extract a first blood vessel diameter from the partial distribution 432*a* for the first area of the comparison area of the distribution 430 of blood vessel diameters. The first blood vessel diameter may be a value representing the blood vessel diameter of the first area and may extract, for example, the median value of the partial distribution 432*a* for the first area as the first blood vessel diameter. In FIG. 4, when the first area corresponds to a more proximal blood vessel than the blood vessel of the stenosis area, the median value of the partial distribution 432*a* may be extracted as the first blood vessel diameter $RVD_{proximal}$ representing a blood vessel diameter of the proximal blood vessel.

The blood vessel analysis apparatus may extract a second blood vessel diameter from the partial distribution 432*b* for the second area of the comparison area of the distribution 430 of blood vessel diameters. The second blood vessel diameter may be a value representing the blood vessel diameter of the second area and may extract, for example, the median value of the partial distribution 432*b* for the second area as the second blood vessel diameter. In FIG. 4, when the second area corresponds to a more distal blood vessel than the blood vessel of the stenosis area, the median value of the partial distribution 432*b* may be extracted as the second blood vessel diameter $RVD_{distal}$ representing a blood vessel diameter of the distal blood vessel.

In the present disclosure, although the first blood vessel diameter and the second blood vessel diameter are described as the median value of the partial distribution, examples are not limited thereto. For example, the blood vessel analysis apparatus may extract a combination of one or more of the minimum value, mode, maximum value, and mean of the partial distribution as the blood vessel diameter (e.g., the first blood vessel diameter and the second blood vessel diameter).

The blood vessel analysis apparatus may calculate the RVD based on the blood vessel diameter corresponding to the comparison area extracted from the distribution of blood vessel diameters. For example, the blood vessel analysis apparatus may calculate the RVD based on the first blood vessel diameter and the second blood vessel diameter. For example, the blood vessel analysis apparatus may calculate the mean of the first and second blood vessel diameters as the RVD. For example, the blood vessel analysis apparatus may calculate the RVD according to Equation 1 below.

$$RVD_{mean} = \frac{RVD_{proximal} - RVD_{distal}}{2} \qquad \text{Equation 1}$$

Here, $RVD_{proximal}$ denotes the first blood vessel diameter, $RVD_{distal}$ denotes the second blood vessel diameter, and $RVD_{mean}$ denotes the RVD.

The blood vessel analysis apparatus may determine a stenosed blood vessel diameter calculated in the stenosis area, based on the distribution of the blood vessel diameters in the stenosis area. The stenosed blood vessel diameter may be a value representing the blood vessel diameter of the stenosis area and may correspond to a blood vessel (e.g., a stenosed blood vessel portion) of the stenosis area. For example, as illustrated in FIG. 4, the blood vessel analysis apparatus may extract a minimum value of the partial distribution 431 for the stenosis area as the stenosed blood vessel diameter. In FIG. 4, the stenosed blood vessel diameter may be illustrated as a minimum luminal diameter (MLD).

In the present disclosure, although the stenosed blood vessel diameter is described as a minimum value of the partial distribution 431 for the stenosis area, examples are not limited thereto. For example, the blood vessel analysis apparatus may extract a combination of one or more of the median value, mode, maximum value and mean of the partial distribution as the stenosed blood vessel diameter.

The blood vessel analysis apparatus may calculate the stenosis score based on a comparison result of the RVD and the stenosed blood vessel diameter. For example, the blood vessel analysis apparatus may calculate the stenosis score based on a difference between the RVD and the stenosed blood vessel diameter. The blood vessel analysis apparatus may calculate a ratio of the difference between the RVD and the stenosed blood vessel diameter as the stenosis score. The stenosis score may be calculated as a value in a range of 0 or more and 1 or less, and the degree of stenosis of the stenosed portion is greater than that of another portion (e.g., a blood vessel of the comparison area) as the stenosis score increases. Conversely, as the stenosis score decreases, the degree of stenosis of the stenosed portion is less than that of the other portion (e.g., the blood vessel of the comparison area).

According to an embodiment, the blood vessel analysis apparatus may calculate the stenosis score according to Equation 2 below.

$$ SS = \frac{RVD_{mean} - MLD}{RVD_{mean}} \qquad \text{Equation 2} $$

Here, $RVD_{mean}$ denotes the RVD, MLD denotes the stenosed blood vessel diameter, and SS denotes the stenosis score.

Figure 5:
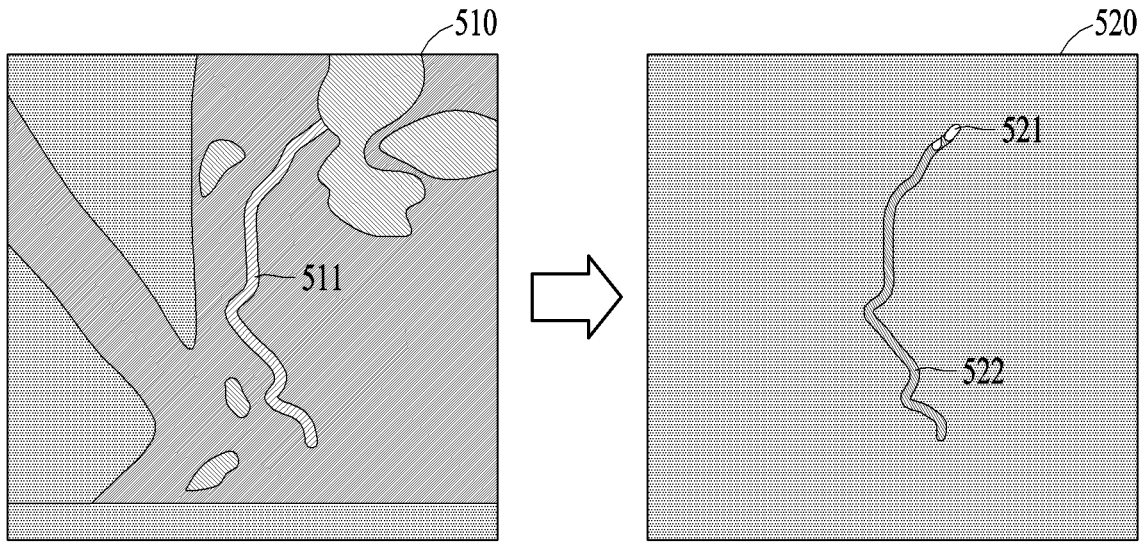
FIG. 5 is a diagram illustrating an operation of calculating a calcification score based on a machine learning model by the blood vessel analysis apparatus according to an embodiment.

FIG. 5 is a diagram illustrating an operation of calculating a calcification score based on a machine learning model by the blood vessel analysis apparatus according to an embodiment.

The blood vessel analysis apparatus according to an embodiment may detect a blood vessel area 511 by applying the machine learning model to a blood vessel image 510.

The blood vessel analysis apparatus may detect a calcification area 521 of the blood vessel area 511. The blood vessel analysis apparatus may determine whether each of the pixels of the blood vessel image 510 belongs to the calcification area 521 by using a pixel value of each of the pixels.

According to an embodiment, the blood vessel analysis apparatus may determine a threshold value to divide the blood vessel area 511 into the calcification area 521 and an area 522 (e.g., a normal area where calcification is not progressed) different from the calcification area 521. The blood vessel analysis apparatus may detect the calcification area 521 by comparing a pixel value of the blood vessel image 510 with the threshold value. A calcified point of a blood vessel in the blood vessel area 511 may have a pixel value greater than that of a non-calcified point (e.g., a normal point). The blood vessel analysis apparatus may classify a pixel having a pixel value exceeding the determined threshold value as a calcified pixel. The blood vessel analysis apparatus may classify a pixel having a pixel value less than or equal to the determined threshold value as a non-calcified pixel (e.g., a normal pixel). The blood vessel analysis apparatus may detect the calcification area 521 having pixels that are classified as calcified pixels.

The blood vessel analysis apparatus may calculate the calcification score based on the blood vessel area 511 and the calcification area 521. The calcification score may be the degree of calcification of a blood vessel.

According to an embodiment, the blood vessel analysis apparatus may calculate the calcification score based on a ratio of the calcification area 521 to the blood vessel area 511. For example, the blood vessel analysis apparatus may calculate the ratio of the number of pixels belonging to the calcification area 521 to the number of pixels of the blood vessel area 511 as the calcification score. As another example, the blood vessel analysis apparatus may calculate the ratio of the number of the pixels belonging to the calcification area 521 to the number of pixels of the area 522 (e.g., the remaining area excluding the calcification area 521 of the blood vessel area 511) different from the calcification area 521 as the calcification score.

For example, the blood vessel analysis apparatus may calculate the calcification score according to Equation 3 below.

$$ CAC \text{ score} = \frac{\text{Calcified counts}}{\text{total vessel counts}} \qquad \text{Equation 3} $$

Here, total vessel counts denotes the number of pixels belonging to a blood vessel area, Calcified counts denotes the number of pixels belonging to a calcification area, and CAC score denotes the calcification score.

The blood vessel analysis apparatus may visualize the detected calcification area 521. For example, the blood vessel analysis apparatus may output a graphic representation indicating the calcification area 521 to the blood vessel image 510. The blood vessel analysis apparatus may output graphic representations respectively indicating the blood vessel area 511 and the calcification area 521 to the blood vessel image 510.

Figure 6:
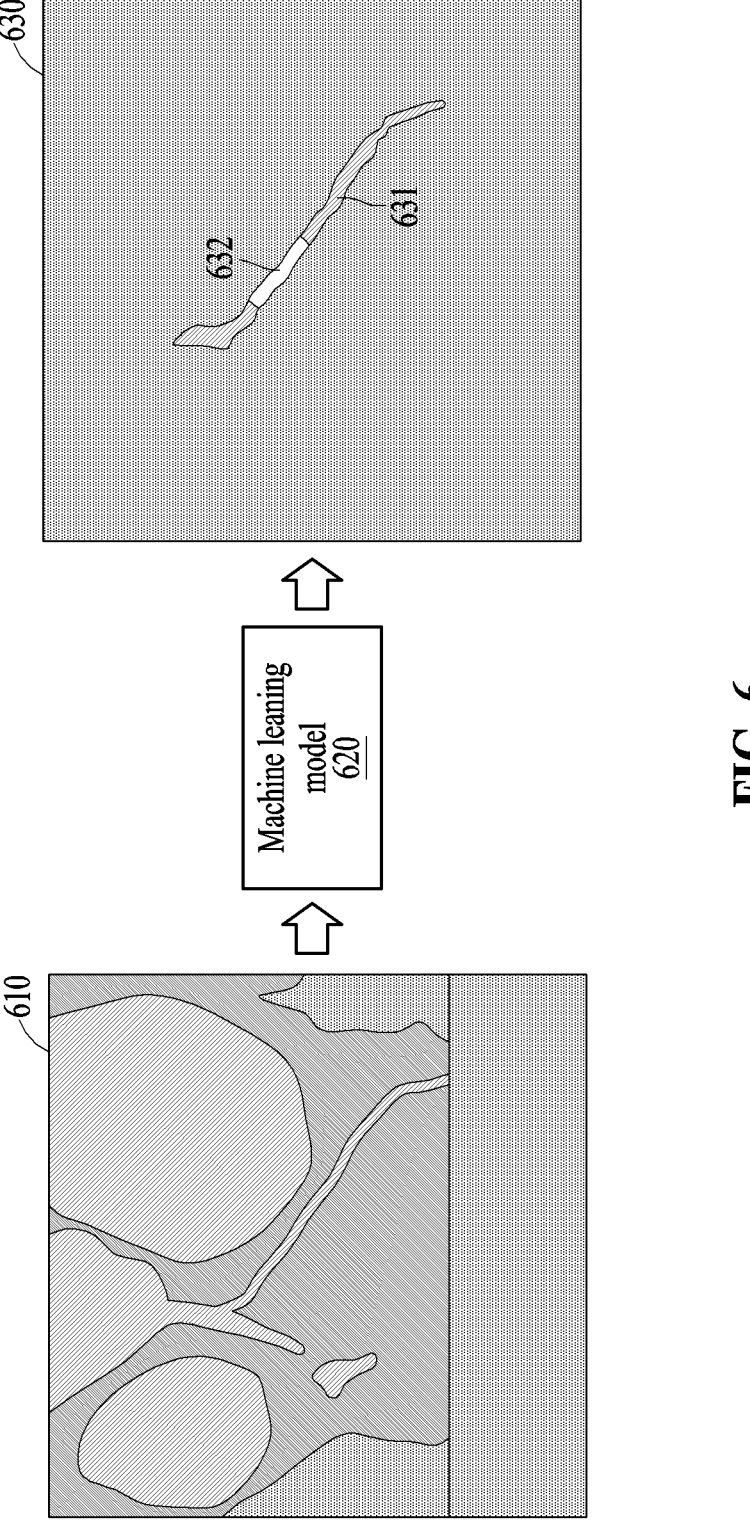
FIG. 6 is a diagram illustrating an operation of detecting a plaque area based on a machine learning model by the blood vessel analysis apparatus according to an embodiment.

FIG. 6 is a diagram illustrating an operation of detecting a plaque area based on a machine learning model 620 by the blood vessel analysis apparatus according to an embodiment.

The blood vessel analysis apparatus according to an embodiment may detect a plaque area 632 together with a blood vessel area 631 by applying the machine learning model 620 to a blood vessel image 610. The plaque area 632 may be an area corresponding to a vulnerable plaque.

The machine learning model 620 may include a segmentation model that is trained to detect a blood vessel area corresponding to a blood vessel by being applied to the blood vessel image. The machine learning model 620 may be trained to further detect a plaque area corresponding to a vulnerable plaque of the blood vessel together with the blood vessel area. According to an embodiment, the machine learning model 620 may be implemented as a neural network model. For example, the machine learning model 620 may be implemented as a model based on a U-Net.

According to an embodiment, the blood vessel analysis apparatus may detect the blood vessel area, a stenosis area, and the plaque area by using a plurality of machine learning models 620. The blood vessel analysis apparatus may detect the blood vessel area and the stenosis area by applying a first machine learning model 620 to the blood vessel image. The blood vessel analysis apparatus may detect the blood vessel area and the plaque area by applying a second machine learning 620 model to the blood vessel image. The first machine learning model 620 and the second machine learning model 620 may have the same structure but different weights. For example, the first machine learning model 620 and the second machine learning model 620 may each be implemented as a model based on the U-Net. The first machine learning model 620 may be separately trained from the second machine learning model 620. In the present disclosure, although the machine learning model 620 used to detect the stenosis area is described as a model different from a machine learning model 620 used to detect the plaque area, examples are not limited thereto. For example, the blood vessel analysis apparatus may detect the blood vessel area, the stenosis area, and the plaque area by applying machine learning model 620 to the blood vessel image.

The examples described herein may be implemented by using a hardware component, a software component and/or a combination thereof. A processing device may be implemented using one or more general-purpose or special-purpose computers, such as, for example, a processor, a controller and an arithmetic logic unit (ALU), a digital signal processor (DSP), a microcomputer, a field-programmable gate array (FPGA), a programmable logic unit (PLU), a microprocessor, or any other device capable of responding to and executing instructions in a defined manner. The processing device may run an operating system (OS) and one or more software applications that run on the OS. The processing device also may access, store, manipulate, process, and create data in response to execution of the software. For the purpose of simplicity, the description of a processing device is used as singular; however, one skilled in the art will appreciate that a processing device may include multiple processing elements and multiple types of processing elements. For example, the processing device may include a plurality of processors, or a single processor and a single controller. In addition, different processing configurations are possible, such as parallel processors.

The software may include a computer program, a piece of code, an instruction, or some combination thereof, to independently or uniformly instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network-coupled computer systems so that the software is stored and executed in a distributed fashion. The software and data may be stored by one or more non-transitory computer-readable recording mediums.

The methods according to the above-described examples may be recorded in non-transitory computer-readable media including program instructions to implement various operations of the above-described examples. The media may also include, alone or in combination with the program instructions, data files, data structures, and the like. The program instructions recorded on the media may be those specially designed and constructed for the purposes of examples, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher-level code that may be executed by the computer using an interpreter.

The above-described devices may act as one or more software modules in order to perform the operations of the above-described examples, or vice versa.

As used herein, "A or B," "at least one of A and B," "at least one of A or B," "A, B or C," "at least one of A, B and C," and "at least one of A, B, or C," each of which may include any one of the items listed together in the corresponding one of the phrases, or all possible combinations thereof.

As described above, although the examples have been described with reference to the limited drawings, a person skilled in the art may apply various technical modifications and variations based thereon. For example, suitable results may be achieved if the described techniques are performed in a different order and/or if components in a described system, architecture, device, or circuit are combined in a different manner and/or replaced or supplemented by other components or their equivalents.

Therefore, the scope of the disclosure is defined not by the detailed description, but by the claims and their equivalents, and all variations within the scope of the claims and their equivalents are to be construed as being included in the disclosure.

What is claimed is:

1. A method performed by an apparatus for analyzing a blood vessel, the method comprising:
   receiving a blood vessel image from an input unit;
   preprocessing, with a processor, the blood vessel image to determine a target blood vessel of blood vessels in the blood vessel image, wherein the target blood vessel in the blood vessel image is emphasized by blurring surrounding structure in the blood vessel image;
   detecting, with the processor a blood vessel area corresponding to the target blood vessel and a stenosis area corresponding to a stenosed portion of the target blood vessel, based on a machine learning model, from the blood vessel image;
   determining, with the processor and the machine learning model, a partial area of the blood vessel area to be a comparison area for the stenosis area, based on a length of the stenosis area, by determining a first area and a second area each on respective sides of the stenosis area in a longitudinal direction of the target blood vessel to be the comparison area, wherein a median value of a blood vessel diameter of the second area is less than a median value of a blood vessel diameter of the first area; and
   calculating, with the processor, a stenosis score indicating a degree of stenosis of a blood vessel of the stenosis area compared to a blood vessel of the comparison area, based on a distribution of blood vessel diameters in the longitudinal direction of the target blood vessel in the blood vessel area.

2. The method of claim 1, wherein the detecting the blood vessel area and the stenosis area comprises:
   detecting an area comprising a blood vessel diameter decreasing in the longitudinal direction of the target blood vessel as the comparison area in an area different from the stenosis area of the blood vessel area.

3. The method of claim 1, wherein the determining the comparison area comprises:

determining a partial centerline based on a partial reference line corresponding to the stenosis area of a reference line of the target blood vessel; and determining an area corresponding to the determined partial centerline to be the comparison area.

4. The method of claim 1, wherein the determining the comparison area further comprises:

determining the comparison area corresponding to a normal blood vessel adjacent to the stenosed portion of the stenosis area of the blood vessel area.

5. The method of claim 1, wherein determining the comparison area further comprises:

determining the first area corresponding to a more proximal blood vessel than the target blood vessel of the stenosis area and the second area corresponding to a more distal blood vessel than the target blood vessel of the stenosis area to be the comparison area.

6. The method of claim 1, wherein the calculating the stenosis score comprises:

extracting blood vessel diameters corresponding to the stenosis area and the comparison area from the distribution of the blood vessel diameters; and calculating the stenosis score by using the extracted blood vessel diameters.

7. The method of claim 1, wherein the calculating the stenosis score further comprises:

determining a reference vessel diameter estimated as a diameter of a normal blood vessel in the stenosis area, based on the distribution of the blood vessel diameters in the comparison area;

determining a stenosed blood vessel diameter calculated in the stenosis area, based on the distribution of the blood vessel diameters in the stenosis area; and calculating the stenosis score based on a comparison result of the reference vessel diameter and the stenosed blood vessel diameter.

8. The method of claim 1, wherein the calculating the stenosis score further comprises:

extracting a first blood vessel diameter from a partial distribution for the first area of the comparison area of the distribution of the blood vessel diameters;

extracting a second blood vessel diameter from a partial distribution for the second area of the comparison area of the distribution of the blood vessel diameters;

calculating a reference vessel diameter corresponding to a normal blood vessel, based on the first blood vessel diameter and the second blood vessel diameter;

extracting a minimum value of a partial distribution for the stenosis area of the distribution of the blood vessel diameters as a stenosed blood vessel diameter corresponding to the stenosis area; and calculating the stenosis score based on a comparison result of the calculated reference vessel diameter and the extracted stenosed blood vessel diameter.

9. The method of claim 1, further comprising:

detecting a calcification area of the blood vessel area based on a pixel value of the blood vessel image; and calculating a calcification score indicating a degree of calcification of the target blood vessel, based on a ratio of the calcification area to the blood vessel area.

10. The method of claim 9, further comprising outputting a graphic representation indicating the calcification area to the blood vessel image.

11. The method of claim 1, further comprising detecting a plaque area corresponding to a vulnerable plaque, together with the blood vessel area, by applying the machine learning model to the blood vessel image.

12. An apparatus for analyzing a blood vessel, the apparatus comprising:

an input unit; and a processor configured to preprocess a blood vessel image received by the input unit to determine a target blood vessel of blood vessels in the blood vessel image, wherein the target blood vessel in the blood vessel image is emphasized by blurring surrounding structure in the blood vessel image, wherein the processor is configured to detect a blood vessel area corresponding to the target blood vessel and a stenosis area corresponding to a stenosed portion of the target blood vessel, based on a machine learning model, from the blood vessel image, determine with the machine learning model a partial area of the blood vessel area to be a comparison area for the stenosis area, based on a length of the stenosis area by determining a first area and a second area each on respective sides of the stenosis area in a longitudinal direction of the target blood vessel to be the comparison area, wherein a median value of a blood vessel diameter of the second area less than a median value of a blood vessel diameter of the first area, and calculate, using the processor, a stenosis score indicating a degree of stenosis of a blood vessel of the stenosis area compared to a blood vessel of the comparison area.

13. The apparatus of claim 12, wherein the processor is further configured to detect an area comprising a blood vessel diameter decreasing in the longitudinal direction of the target blood vessel as the comparison area in an area different from the stenosis area of the blood vessel area.

14. The apparatus of claim 12, wherein the processor is further configured to determine a partial centerline based on a partial reference line corresponding to the stenosis area of a reference line of the target blood vessel, and determine an area corresponding to the determined partial centerline to be the comparison area.

15. The apparatus of claim 12, wherein the processor is further configured to determine the comparison area corresponding to a normal blood vessel adjacent to the stenosed portion of the stenosis area of the blood vessel area.

16. The apparatus of claim 12, wherein the processor is further configured to extract blood vessel diameters corresponding to the stenosis area and the comparison area from the distribution of the blood vessel diameters, and calculate the stenosis score by using the extracted blood vessel diameters.

17. The apparatus of claim 12, wherein the processor is further configured to determine a reference vessel diameter estimated as a diameter of a normal blood vessel in the stenosis area, based on the distribution of the blood vessel diameters in the comparison area, determine a stenosed blood vessel diameter calculated in the stenosis area, based on the distribution of the blood vessel diameters in the stenosis area, and calculate the stenosis score based on a comparison result of the reference vessel diameter and the stenosed blood vessel diameter.

18. The apparatus of claim 12, wherein the processor is further configured to extract a first blood vessel diameter from a partial distribution for the first area of the comparison area of the distribution of the blood vessel diameters, extract a second blood vessel diameter from a partial distribution for the second area of the comparison area of the distribution of the blood vessel diameters, calculate a reference vessel diameter corresponding to a normal blood vessel, based on the first blood vessel diameter and the second blood vessel diameter, extract a minimum value of a partial distribution for the stenosis area of the distribution of the blood vessel diameters as a stenosed blood vessel diameter corresponding to the stenosis area, and calculate the stenosis score based on a comparison result of the calculated reference vessel diameter and the extracted stenosed blood vessel diameter.

\* \* \* \* \*